United States Patent [19]

Simpson

[11] E Re. 31,061

[45] Reissued Oct. 19, 1982

[54] 5-AMINO OR SUBSTITUTED AMINO-7-PHENYL OR SUBSTITUTED PHENYL-2,3-DIHYDRO-1H-1,4-DIAZEPINES

[75] Inventor: William R. Simpson, Mendham, N.J.

[73] Assignee: Sandoz, Inc., East Hanover, N.J.

[21] Appl. No.: 134,444

[22] Filed: Mar. 27, 1980

Related U.S. Patent Documents

Reissue of:

[64] Patent No.: 4,096,140
Issued: Jun. 20, 1978
Appl. No.: 725,440
Filed: Sep. 22, 1976

U.S. Applications:

[63] Continuation-in-part of Ser. No. 528,344, Nov. 29, 1974, abandoned, which is a continuation-in-part of Ser. No. 456,017, Mar. 29, 1974, Pat. No. 3,929,884.

[51] Int. Cl.[3] ..... C07D 243/06; A61K 31/55

[52] U.S. Cl. ..... 260/239 BC; 260/243.3; 260/244.4; 424/244; 424/250; 424/267; 424/274; 549/435; 548/518

[58] Field of Search ..... 260/239 BC

[56] References Cited

FOREIGN PATENT DOCUMENTS 1512149 12/1967 France ..... 260/239 BC
1540744 8/1968 France ..... 260/239 BC

OTHER PUBLICATIONS

Hofmann et al., J. Chem. Eng. Data, 10, pp. 188-190,(1965).
Hofmann et al., J. Org. Chem., 27, 3565-3568 (1962).
Gaether, J., Hetercyclic Chem., 8, pp. 519-521 (1971).
Staab et al., Chem. Ber., 98, pp. 2701-2714 (1965).
Gorringe et al., Chem. Ind. (London), 1968, pp. 130-131, 1160.
Gorringe et al., J. Chem. Soc. [C] 1970, pp. 617-620.
Ried et al., Chem. Benichte 87, 1811-1814 (1954).
Cleghorn et al., J. Chem. Soc. B 1971, 1615-1617.
Gorringe et al., J. Chem. Soc. C 1969, 1081-1084.
Gorringe et al., J. Chem. Soc. C 1969, 1449-1456.

*Primary Examiner*—David B. Springer
*Attorney, Agent, or Firm*—Gerald D. Sharkin; Richard E. Vila; Melvyn M. Kassenoff

[57] ABSTRACT

Compounds of the formula

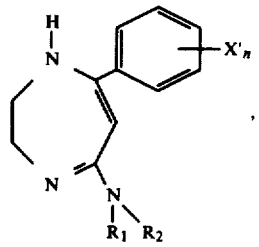

wherein $R_1$ is hydrogen, alkyl of 1 to 6 carbon atoms or amino, $R_2$ is hydrogen or alkyl of 1 to 6 carbon atoms, with the provisos that (1) at least one of $R_1$ and $R_2$ is not a tertiary alkyl group and (2) $R_2$ is hydrogen when $R_1$ is amino, or $R_1$ and $R_2$ taken together and with the nitrogen atom to which they are joined are pyrrolidino, piperidino or N'-2-hydroxyethylpiperazino, each X' is independently alkyl or 1 to 4 carbon atoms, alkoxy of 1 to 4 carbon atoms or halo, or two X's on adjacent carbon atoms together are methylenedioxy, and n is 0, 1, 2 or 3, and the pharmaceutically acceptable acid addition salts thereof, are useful as anti-obesity and anti-diabetic agents. The compounds wherein $R_1$ is alkyl and $R_2$ is hydrogen are synthesized by a two-step synthesis from 2-alkyl-5-arylisoxazolium salts and ethylenediamine. The compounds wherein $R_1$ and $R_2$ are hydrogen are synthesized by cleaving the t-butyl group from the corresponding compounds wherein $R_1$ is t-butyl and $R_2$ is hydrogen. The compounds wherein $R_1$ is amino are synthesized from the corresponding compounds wherein $R_1$ is hydrogen or alkyl. All of the compounds are synthesized by reacting ammonia, a suitable amine or hydrazine with a compound of the formula

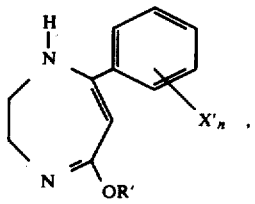

wherein R' is primary or secondary alkyl of 1 to 4 carbon atoms.

32 Claims, No Drawings

5-AMINO OR SUBSTITUTED AMINO-7-PHENYL OR SUBSTITUTED PHENYL-2,3-DIHYDRO-1H-1,4-DIAZEPINES

Matter enclosed in heavy brackets [ ] appears in the original patent but forms no part of this reissue specification; matter printed in italics indicates the additions made by reissue.

This application is *an application for reissue of U.S. Pat. 4,096,140, issued on June 20, 1978 on application Ser. No. 725,440, filed Sept. 22, 1976, which* is a continuation-in-part of application Ser. No. 528,344, filed on Nov. 29, 1974 and now abandoned, which in turn is a continuation-in-part of application Ser. No. 456,017, filed on March 29, 1974 and now U.S. Pat. No. 3,929,884.

This invention relates to compounds of the formula (I)

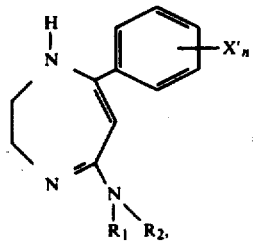

wherein $R_1$ is hydrogen, alkyl of 1 to 6 carbon atoms or amino, $R_2$ is hydrogen or alkyl of 1 to 6 carbon atoms, with the provisos that (1) at least one of $R_1$ and $R_2$ is not a tertiary alkyl group and (2) $R_2$ is hydrogen when $R_1$ is amino, or $R_1$ and $R_2$ taken together and with the nitrogen atom to which they are joined are pyrrolidino, piperidino or N'-2-hydroxyethylpiperazino, each X' is independently alkyl of 1 to 4 carbon atoms, alkoxy of 1 to 4 carbon atoms or halo, or two X's on adjacent carbon atoms together are methylenedioxy, and n is 0, 1, 2 or 3, and the pharmaceutically acceptable acid addition salts thereof, processes for their synthesis, intermediates useful in their synthesis and their use as anti-obesity and antidiabetic agents as well as to pharmaceutical compositions useful for the treatment of obesity and diabetes.

The preferred compounds of this application are those of Formula I wherein $R_1$ is hydrogen, alkyl of 1 to 6 carbon atoms or amino, and $R_2$ is hydrogen, and the pharmaceutically acceptable acid addition salts thereof, and particularly those of this group wherein each X' is independently alkyl of 1 to 3 carbon atoms, methoxy, ethoxy, chloro or bromo, and n is 0, 1 or 2, and the pharmaceutically acceptable acid addition salts thereof.

Still more preferred are the compounds of the formula (II)

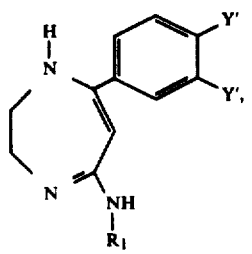

wherein $R_1$ is hydrogen, alkyl of 1 to 6 carbon atoms or amino, and each Y' is independently hydrogen, methyl, ethyl, methoxy or ethoxy, and the pharmaceutically acceptable acid addition salts thereof, and especially the compounds of Formula II wherein each Y' is independently hydrogen, methyl or methoxy, and the pharmaceutically acceptable acid addition salts thereof.

Also preferred are the compounds of Formula II wherein $R_1$ is hydrogen or t-butyl, and the pharmaceutically acceptable acid addition salts thereof, and especially the compounds of this group wherein each Y' is independently hydrogen, methyl or methoxy, and the pharmaceutically acceptable acid addition salts thereof.

Most preferred are the compounds of the formula (III)

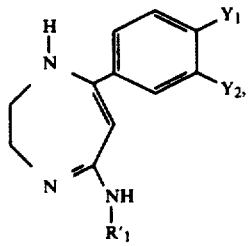

wherein $R_1'$ is hydrogen or t-butyl, $Y_1$ is hydrogen, methyl or methoxy, and $Y_2$ is hydrogen or methyl, and the pharmaceutically acceptable acid addition salts thereof, and especially the compounds of this group wherein $R_1'$ is hydrogen, and the pharmaceutically acceptable acid addition salts thereof.

Representative of the compounds of Formula I are the compounds of the formula (IV)

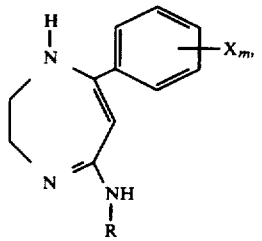

wherein R is alkyl of 1 to 6 carbon atoms,
each X is independently alkyl of 1 to 4 carbon atoms, alkoxy of 1 to 4 carbon atoms or halo, and
m is 0, 1 or 2,
and the pharmaceutically acceptable acid addition salts thereof,
and the compounds of Formula IV
wherein m is 0 or 1,
and the pharmaceutically acceptable acid addition salts thereof.

The preferred compounds of Formula IV are those of the formula (V)

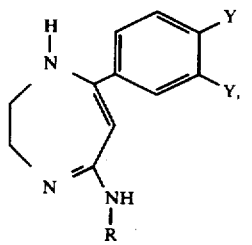

wherein R is alkyl of 1 to 6 carbon atoms, and
each Y is hydrogen, alkyl of 1 to 3 carbon atoms, methoxy, ethoxy, chloro or bromo,
with the proviso that at least one Y is hydrogen,
and the pharmaceutically acceptable acid addition salts thereof,
and especially the compounds of this group
wherein each Y is hydrogen,
and the pharmaceutically acceptable acid addition salts thereof.

The most preferred compounds of Formula IV are the compound
wherein R is t-butyl, and
m is 0,
and its pharmaceutically acceptable acid addition salts.

The term "halo" means chloro, bromo or fluoro.

All pharmaceutically acceptable acid addition salts of the compounds of Formula I (i.e., those salts which do not significantly increase the toxicity of the basic compound) are included within the scope of this invention. Included are salts with inorganic acids, e.g., the hydrochloride, hydrobromide, hydroiodide, phosphate (including hydrogen phosphates), methaphosphate, sulfate (including hydrogen sulfate) and perchlorate salts and salts with organic acids, e.g., the acetate, propionate, tartarate, citrate, gluconate, fumarate, malate, maleate, methanesulfonate, ethanesulfonate, benzenesulfonate and p-toluenesulfonate salts. Also included are the tetrafluoroborate salts.

Generally, the acid addition salts are preferable to the free base since they are easier to isolate in crystalline form and are more stable. Furthermore, in solution the free bases tend to pick up carbon dioxide from the atmosphere and become carbonate or bicarbonate salts.

Among the preferred salts are the methanesulfonate and perchlorate salts, particularly the former.

The compounds of Formula I wherein $R_1$ is alkyl and $R_2$ is hydrogen can be synthesized from isoxazolium salts and ethylenediamine by a two-step synthesis.

In Step A of the synthesis, an isoxazolium salt of the formula (VI)

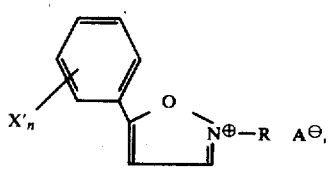

wherein R is alkyl of 1 to 6 carbon atoms, and
X' and n are as defined above in connection with Formula I, and
$A^{\ominus}$ is a non-interfering anion, e.g., perchlorate, tetrafluoroborate, methylsulfate, ethylsulfate, bisulfate, chloride, bromide or iodide,
is reacted with ethylenediamine ($NH_2—CH_2CH_2—NH_2$) in an inert organic solvent at a temperature of −10°-40° C., preferably 10°-35° C., to obtain a compound of the formula (VII)

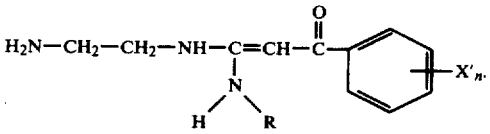

The preferred compounds of Formula VII are those of the formula (VII A)

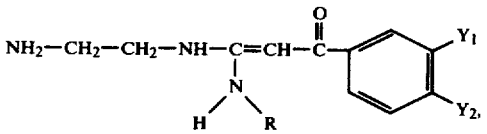

wherein R is alkyl of 1 to 6 carbon atoms,
$Y_1$ is hydrogen, methyl or methoxy, and
$Y_2$ is hydrogen or methyl,
and especially those of this group
wherein R is methyl, ethyl or t-butyl.

As is well-known to those in the art, the reaction time necessary is inversely related to the reaction temperature, i.e., the higher the reaction temperature, the shorter the reaction time. It is, therefore, impossible to give a precise reaction time. However, a reaction time of 20–120 minutes is generally acceptable with a reaction time of 30–90 minutes being preferred.

The reaction solvent is not critical. Any non-nucleophilic organic solvent in which the reactants are soluble and having a boiling point at or above the desired reaction temperature may be used. An inert solvent is one that does not react with either of the starting materials under the reaction conditions employed. Among the inert solvents that are suitable are liquid halogenated lower alkanes (e.g., methylene chloride, chloroform, 1,2-dichloroethane, 1,2-dibromoethane, 1,1,1-trichloroethane and 1-bromo-2-chloroethane), symmetrical and unsymmetrical dialkyl ethers having a total of at least 5 carbon atoms and preferably no more than 10 carbon atoms, cyclic ethers (e.g., p-dioxane and tetrahydrofuran), lower alkyl nitriles (e.g., acetonitrile), lower alkyl esters of lower alkanoic acids, N,N-dimethylacetamide and formic acid amides (e.g., formamide and its N-monolower alkyl and N,N-dilower alkyl derivatives such as N-ethylformamide, N,N-dimethylformamide, N,N-diethylformamide and N-methyl-N-ethylformamide) and mixtures of these solvents. The halogenated lower alkanes are preferred with methylene chloride being particularly preferred.

While the molar ratio of ethylenediamine to isoxazolium salt can be as low as 1:1, it is preferably at least 1.5:1 in order to minimize reaction of the compound of Formula VII with another isoxazolium cation. However, a large molar excess of ethylenediamine is generally employed, e.g., 2 to 10 mols of ethylenediamine per mol of isoxazolium salt.

Since the reaction is exothermic, the isoxazolium salt is generally added to a solution of ethylenediamine in small portions at a rate such that the temperature of the reaction mixture does not exceed the maximum desired temperature. If necessary, the reaction mixture is cooled during addition of the isoxazolium salt to prevent the temperature from rising precipitously.

Advantageously, the reaction is run under an inert atmosphere (nitrogen, helium, neon, argon, krypton or xenon, or a mixture thereof, preferably nitrogen). However, the use of an inert atmosphere is not essential.

In Step B, a compound of Formula VII is treated with a strong acid to effect cyclization to an acid addition salt of a compound of Formula I. The cyclization is carried out in an inert organic solvent at a temperature of 45°-120° C., preferably 55°-100° C., under an inert atmosphere (nitrogen, helium, neon, argon, krypton or xenon, or a mixture thereof).

As in the case of Step A, a precise reaction time cannot be given because the higher the reaction temperature, the shorter the reaction time. However, a reaction time of 30-180 minutes, preferably 60-120 minutes, is generally employed.

Any inert organic solvent in which the reactant is soluble and which has a boiling point at or above the desired reaction temperature may be employed. As indicated above, an inert solvent is one that does not react with the reactant, i.e., one that does not interfere with the desired intramolecular cyclization. Among the inert solvents that are suitable are lower alkanols (e.g., ethanol, n-propanol, iso-propanol, n-butanol, sec.-butanol and iso-butanol), halogenated lower alkanes (e.g., 1,1,2-trichloroethane and 1,2-dichloroethane), cyclic ethers such as p-dioxane, symmetrical and unsymmetrical dialkyl ethers having a total of at least 5 carbon atoms preferably no more than 10 carbon atoms and formic acid amides (e.g., formamide and its N-monolower alkyl and N,N-dilower alkyl derivatives such as N-ethylformamide, N,N-dimethylformamide, N,N-diethylformamide and N-ethyl-N-methylformamide) and mixtures of these solvents. The preferred solvents are the lower alkanols. The most preferred solvents are ethanol, propanol and isopropanol.

Any strong acid can be used to effect cyclization, e.g., perchloric acid, hydrochloric acid, hydrobromic acid, sulfuric acid, methanesulfonic acid, ethanesulfonic acid, benzenesulfonic acid and p-toluenesulfonic acid. The acid may be employed in any form, e.g., as a concentrated aqueous acid, as a solution in an organic solvent, e.g., a lower alkanol such as ethanol, propanol or iso-propanol, or in undiluted form. For example, perchloric acid is usually used as a 70% aqueous solution, hydrochloric and hydrobromic acids are generally employed as saturated solutions of gaseous hydrogen chloride and hydrogen bromide, respectively, in one of the aforementioned lower alkanols, sulfuric acid is employed as a concentrated liquid, and the aforementioned sulfonic acids are usually used as solids. While as little as one equivalent of the acid can be employed, an excess is generally used. Standard operating procedure is to add sufficient acid to bring the pH to about 0.1 to 6, generally 1 to 4, and preferably 2 to 3, as indicated by moist pH paper.

The two steps of the synthesis can be carried out successively without isolating the intermediate of Formula VII or even combined into a single step. A reaction temperature of 45°-120° C., preferably 55°-80° C., a reaction time of 30-180 minutes, preferably 60-120 minutes, after addition of the isoxazolium salt has been completed, and an inert atomosphere are generally employed for the one-step reaction. The solvents indicated to be useful for Step A of the two-step synthesis are useful for the one-step reaction. However, the two-step synthesis described above is preferred since it gives a cleaner product, i.e., a product that requires less purification.

The isoxazolium salts of Formula VI are known or can be produced by a conventional quaternization of the corresponding isoxazoles with a strong alkylating agent such as triethyloxonium tetrafluoroborate or a mixture of t-butanol and perchloric acid. See, for example, Woodward et al., J. Amer. Chem. Soc. 83, 1007-1009 (1961), Woodward et al., J. Amer. Chem. Soc. 83, 1010-1012 (1961), and Woodward et al., J. Org. Chem. 31, 2039-2040 (1966). The isoxazoles are either known or can be prepared by conventional processes from known precursors.

The acid addition salts of the compounds wherein $R_1$ and $R_2$ are hydrogen are preferably synthesized by cleaving the t-butyl group from an acid addition salt of a compound of Formula I wherein $R_1$ is t-butyl and $R_2$ is hydrogen.

This reaction is most conveniently effected by heating an acid addition salt of a compound of Formula I wherein $R_1$ is t-butyl and $R_2$ is hydrogen at a temperature above its melting point and decomposition temperature (and below its boiling point and the lower of the decomposition temperature and the boiling point of the desired compound) in the presence of a catalytic amount of acid until bubbling (the evolution of isobutylene) commences and continuing the heating until the bubbling ceases. Salts which may be explosive at elevated temperatures, e.g., perchlorate salts, and salts which may otherwise decompose at elevated temperature (except for the desired reaction) should not be employed unless suitable precautions are taken. The methanesulfonate salts are particularly suitable for this reaction.

The reaction is acid catalyzed. Generally, the acid addition salts contain sufficient free acid to catalyze the reaction and, therefore, no additional acid need be added. However, at least a catalytic amount, e.g., 0.01 equivalents, of any acid (excluding, unless suitable precautions are taken, those whose salts may be explosive or otherwise undergo an undesired decomposition) must be added if the starting acid addition salt has been purified to eliminate the presence of free acid. However, more than a catalytic amount (e.g., 0.01-4 equivalents) may be utilized. Preferably, the added acid is identical to the acid portion of the starting acid addition salt.

The t-butyl group of the free bases of Formula I wherein $R_1$ is t-butyl and $R_2$ is hydrogen may be cleaved by converting the free bases into the corresponding acid addition salts in situ. Thus, if a free base is employed, one equivalent plus a catalytic amount of acid must be added to catalyze the cleavage. Suitably, 1.01 equivalents of any acid (excluding, unless suitable precautions are taken, those whose salts may be explosive at elevated temperatures) are employed. However, more than one equivalent (e.g., 1.05–5 equivalents) may be used. Among the preferred acids is methanesulfonic acid.

It is impossible to give a precise reaction temperature and time. However, a temperature of 150°–210° C. and a reaction time of 5–45 minutes are usually effective.

The reaction is preferably run neat. However, any high-boiling inert organic solvent may be employed. Obviously, the solvent should have a boiling point above the reaction temperature.

The obtained acid addition salts may be converted into the corresponding free bases and into other acid addition salts as described infra.

The compounds of Formula I wherein $R_1$ is amino and $R_2$ is hydrogen may be synthesized by reacting the corresponding compounds wherein $R_1$ is hydrogen or alkyl and $R_2$ is hydrogen with hydrazine, preferably anhydrous hydrazine, under an inert atmosphere, preferably nitrogen.

A suitable reaction temperature is the boiling point of hydrazine. However, a temperature as low as 80° C. may also be employed.

Since the reaction time is inversely related to the reaction temperature, a precise reaction time cannot be given. However, a reaction time of 20–180 minutes, preferably 30–60 minutes, is generally suitable.

The reaction is preferably run neat with the excess hydrazine serving as the solvent. However, any inert organic solvent having a boiling point at or above the reaction temperature may be employed.

When a solvent is employed, as little as one mol of hydrazine per mol of starting material can be employed. However, 1.05–2 mols of hydrazine per mol of starting material are generally used. When no solvent is employed, a large molar excess of hydrazine, e.g., 10–1000 mols or more is generally employed.

The compounds of Formula I can be synthesized by reacting a compound of the formula

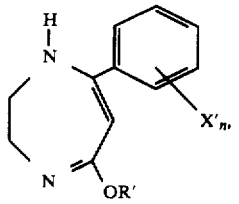

(VIII)

or an acid addition salt thereof, wherein R′ is primary or secondary alkyl of 1 to 4 carbon atoms, preferably primary alkyl of 1 to 4 carbon atoms, and most preferably methyl or ethyl, and X′ and n are defined as in connection with Formula I, with ammonia, a primary or secondary amine or hydrazine, i.e., a compound of the formula

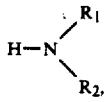

(IX)

wherein $R_1$ and $R_2$ are defined as in connection with Formula I.

Generally the reaction is run by heating a large molar excess of the compound of Formula IX with the compound of Formula VIII, but as little as 1 mol of the compound of Formula IX can be used particularly if a solvent is employed. Usually 1.05–10 mols of the compound of Formula IX per mol of compound of Formula VIII are employed if a solvent is used while 2–1000 mols of the compound of Formula IX per mol of compound of Formula VIII are employed if the reaction is run neat.

With ammonia or a volatile amine, e.g., one with a boiling point lower than about 60° C., the reaction should be run in a reaction bomb. A reaction temperature of 20° to 115° C. may be used, with a temperature of 60° to 105° C. being preferred. A temperature of 100° C. is conveniently used.

With a non-volatile amine or hydrazine the reactants may be heated together under an inert atmosphere as defined above, a nitrogen atmosphere being preferred. The temperature range is 20° to 115° C. with a temperature of 60°–115° C. being preferred. However, the reaction temperature cannot exceed the reflux temperature of the reaction mixture and is preferably the reflux temperature.

As usual, a precise reaction time cannot be given since it is inversely related to the reaction temperature. However, a reaction time of 5 minutes to 3 hours, preferably 10 minutes to 2 hours, is usually adequate.

The excess amine serves as the reaction solvent, i.e., the reaction is preferably run neat. However, any inert organic solvent having a boiling point above the desired reaction temperature may be employed. As is self-evident, the solvent must be non-nucleophilic.

The preferred compounds of Formula VIII are those of the formula

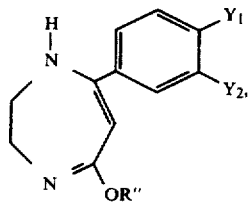

(VIII A)

wherein R″ is methyl or ethyl, $Y_1$ is hydrogen, methyl or methoxy, and $Y_2$ is hydrogen or methyl, and the acid addition salts thereof (e.g., the aforementioned pharmaceutically acceptable acid addition salts).

The preferred compounds of Formula IX are those wherein $R_1$ is hydrogen, alkyl of 1 to 6 carbon atoms or amino, and $R_2$ is hydrogen, and especially those of this group wherein $R_1$ is hydrogen, methyl, ethyl or t-butyl.

The compounds of Formula VIII are synthesized by reacting a compound of the formula

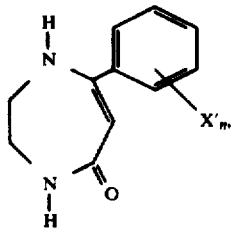

(X)

wherein X' and n are as defined in connection with Formula I, with a trialkyloxonium tetrafluoroborate, preferably trimethyloxonium or triethyloxonium tetrafluoroborate, in an inert organic solvent at a temperature of 0°-30° C., preferably 20°-25° C., with cooling if necessary. It is preferable, but not essential, to employ an inert atmosphere, e.g., nitrogen. The reaction is usually carried out by adding the trialkyloxonium tetrafluoroborate to a solution or suspension of the compound of Formula X portionwise over a period of time so as to maintain the reaction temperature within the desired range. An addition period of 15 minutes to 1 hour, for example 20 to 30 minutes, is typical. Upon completion of the addition, the reaction mixture is usually stirred for an additional 10-60 minutes to complete the reaction.

Any inert organic solvent may be used, i.e., any organic solvent that does not react with either of the starting materials under the reaction conditions employed. It is not necessary that the reactants be completely soluble in the solvent; however, they must be at least partially soluble therein. Among the inert solvents that are suitable are liquid halogenated lower alkanes (e.g., methylene chloride, 1,2-dichloroethane, 1,2-dibromoethane, 1,1,1-trichloroethane and 1-bromo-2-chloroethane). Methylene chloride is particularly preferred.

The molar ratio of trialkyloxonium tetrafluoroborate to compound of Formula X is usually 1:1. However, a slight molar excess, e.g., 5%, of the trialkyloxonium compound can be employed.

The compound of Formula X wherein n is 0 is known. See Ried et al., Chem. Ber. 87, 1811-1814 (1954), and Hofmann et al., J. Org. Chem. 27, 3565-3567 (1962). Other compounds of Formula X are disclosed in Hofmann et al., J. Chem. Eng. Data 10(2), 188-190 (1965). The other compounds of Formula X can be synthesized by processes analogous to those of these publications.

[Alternatively, the compounds of Formula X can be synthesized by cyclizing a compound of the formula]

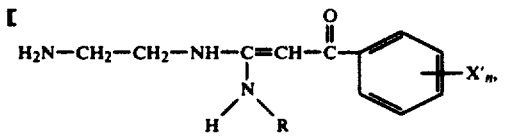

(VII)

[wherein X' and n are as defined as in connection with Formula I, and

R is alkyl of 1 to 6 carbon atoms, at a temperature of 100° to 150° C. in an inert organic solvent free of acid. An inert atmosphere (i.e., nitrogen, helium, argon, neon, krypton or xenon, or a mixture thereof) need not be used. However, it is preferable to employ one, e.g., a nitrogen atmosphere.]

[A precise reaction time cannot be given since the reaction time is inversely related to the reaction temperature. However, a reaction time of 1-5 hours, preferably 1½-3 hours, is usually employed.]

[Any inert organic solvent in which the reactant is soluble and which has a boiling point at or above the desired reaction temperature may be employed. An inert solvent is one that does not react with the desired intramolecular cyclization and cleavage. Among the solvents that may be employed are liquid hydrocarbons such as benzenes having 1 to 3 lower alkyl groups (e.g., o-xylene, m-xylene and p-xylene, and mixtures thereof), nitrobenzene and formic acid amides (e.g., formamide and its N-monolower alkyl and N,N-dilower alkyl derivatives such as N-methylformamide and N,N-dimethylformamide), the alkylbenzenes being preferred.]

The obtained acid addition salts of the compounds of Formula I can be converted to other acid addition salts and to the free base (amine) by conventional means. For example, the methanesulfonate salt of Example 4 can be converted into the free base by partition between aqueous 2 N. sodium hydroxide and chloroform. The free bases can in turn be converted into any other acid addition salt by careful acidification with the appropriate acid. Hence, any acid addition salt or free base which for any reason is not suitable for pharmaceutical use may be converted into a pharmaceutically acceptable acid addition salt that is suited for such use.

The compounds of Formula I and their pharmaceutically acceptable acid addition salts are useful for lowering blood sugar levels, i.e., as anti-obesity agents, as indicated by (a) glucose transport tests carried out in male Wistar rats, and as anti-diabetic agents, as indicated by (b) hypoglycemic tests carried out in male ICR mice, (c) anti-hyperglycemic tests carried out in male ICR mice, rats and hamsters and (d) hypoglycemic tests carried out in male ICR mice pre-treated with streptozotocin as well as tests in monkeys. They are, thus, also useful in the treatment of both juvenile diabetes and mature onset diabetes.

(a) Glucose transport test: Male Wistar rats are dosed orally with 10-80 mg./kg. body weight of the test compound after at least 20 hours of fasting. One hour after receiving the drug, each animal is sacrificed and the upper small intestine is removed and washed with glucose-saline. A 5 cm. section of the intestine is everted so that the mucosal surface is on the outside. One end of the segment is tied and the center of the sac so formed is filled with oxygen saturated Kreb's bicarbonate buffer. The other end is then closed to form a sac which is then incubated in 10 ml. of oxygen saturated bicarbonate buffer for 60 minutes at 37° C. Both the outside and inside solutions contain initially 0.3% glucose. At the end of the incubation time, the glucose content of the outer (mucosal) and the inner (serosal) solution is determined using the standard Auto Analyzer procedure. Similar tests are run simultaneously with control animals receiving only the vehicle. The percent inhibition of glucose transport caused by the drug is calculated from the formula $$I = 100 - \left( \frac{S_I - M_I}{S_c - M_c} \times 100 \right),$$

wherein I = percent inhibition, $S_t$ = glucose concentration (mg. %) of serosal fluid at the end of an experiment in the drug-treated animal, $S_c$ = glucose concentration (mg. %) of serosal fluid at the end of an experiment in the control animal, $M_t$ = glucose concentration (mg. %) of mucosal fluid at the end of an experiment in the drug-treated animal, and $M_c$ = glucose concentration (mg. %) of mucosal fluid at the end of an experiment in the control animal.

(b) Hypoglycemic test: 6–8 week old adult male ICR mice having a body weight of 30–35 g. are dosed orally with 75–200 mg./kg. body weight after 16 hours of fasting. A control group receiving 0.5% carboxymethyl cellulose vehicle is run concurrently. Two hours later the mice are anesthetized with sodium hexobarbital (85 mg./kg. i.p.) and blood is collected via cardiac puncture. The blood is placed in an Auto Analyzer cup containing 0.025 cc of a heparin preparation containing 1000 units/ml. and the samples are capped, shaken and kept in an ice bucket. The glucose content of each sample is measured by the standard Auto Analyzer potassium ferric cyanide method (#N-2b). To validate the test a known hypoglycemic standard is included each time the test is run. The activity of the compound is calculated from the formula $$A = \frac{G_c - G_t}{G_c} \times 100,$$

wherein A = % reduction of the glucose concentration of the blood achieved by the test compound, $G_c$ = glucose concentration (mg. %) of the blood of the control animals, and $G_t$ = glucose concentration (mg. %) of the blood of the animals receiving the test compound.

(c) Anti-hyperglycemic test: Procedure (b) is followed with the following modifications: 1½ hours after the mice are dosed with the test compound or the carboxymethyl cellulose vehicle, the mice receive a glucose challenge of 2 g./kg. body weight p.o. (See Laboratory Animal Digest 7 (4), 76 (1972).) with the sodium hexobarbital anesthetization (85 mg./kg. i.p.) occurring 25 minutes later. The blood is collected exactly 30 minutes following administration of the glucose challenge. A known anti-hyperglycemic standard is included each time the test is run to validate it. This test is also run in hamsters at dosages of 5–75, e.g., 10, mg./kg. body weight and in rats at dosages of 25–100, e.g., 40 mg./kg. body weight.

(d) Hypoglycemic test in streptozotocin diabetic mice: Fed 6–8 old adult male ICR mice are given a single i.v. injection in the tail vein of 175 mg./kg. body weight of streptozotocin in citrate buffer at pH 4.5. (To avoid decomposition of the solubilized streptozotocin, the fresh solution is used within 30 minutes.) The streptozotocin pre-treated mice are kept in clean cages with food and water for six days at the end of which they are tested for urinary sugar with Clinistix. Only those mice that show a positive urine Clinistix reaction are dosed orally with 5–200 mg./kg. body weight of the test compound at which time the food is removed from the cages. A control group receiving 0.5% carboxymethyl cellulose vehicle is run concurrently. 2–8 hours, preferably 4 hours, later, the mice are anesthetized with ether and whole blood is collected via cardiac puncture. The blood is placed in an Auto Analyzer cup containing 0.025 cc of a heparin preparation containing 1000 units/ml. and the samples are capped, shaken and kept in an ice bucket. The glucose content of each sample is measured by the standard Auto Analyzer potassium ferric cyanide method (#N-2b). To validate the test a known hypoglycemic standard (active in hosts having juvenile-type diabetes) is included each time the test is run. The activity of the compound is calculated from the formula $$A = \frac{G_c - G_t}{G_c} \times 100,$$

wherein A = % reduction of the glucose concentration of the blood achieved by the test compound, $G_c$ = glucose concentration (mg. %) of the blood of the control animals, and $G_t$ = glucose concentration (mg. %) of the blood of the animals receiving the test compound.

The preferred compounds of this application, e.g., the compounds of Formula I wherein $R_2$ is hydrogen, and the pharmaceutically acceptable acid addition salts thereof, particularly the more preferred compounds of this application, e.g., the compounds of Formula II and the pharmaceutically acceptable acid addition salts thereof, and especially the most preferred compounds, e.g., the compounds of Formula III and the pharmaceutically acceptable acid addition salts thereof, are the compounds that are preferred for the treatment of diabetes (both juvenile and mature onset types). However, it is the compound of Example 13 (Compound XXIII) and, to a somewhat lesser degree, the corresponding free base (the Compound of Example 24; Compound XXXIV) and other pharmaceutically acceptble acid addition salts thereof that are most preferred for the treatment of both juvenile-type and mature onset diabetes.

The precise dosage of the compound of Formula I, or a pharmaceutically acceptable acid addition salt thereof, to be employed depends upon several factors including the severity of the condition being treated, the mode of administration and the particular compound employed. However, in general, satisfactory results in the treatment of either obesity or diabetes are obtained when a compound of Formula I, or a pharmaceutically acceptable acid addition salt thereof, is administered at a daily p.o. dosage of 1–200 mg./kg. body weight or a daily dosage of 75–2000 mg. for most larger mammals. The daily dosage is usually divided into two to four equal portions. A typical oral dosage for the treatment of larger mammals having juvenile or mature onset diabetes is 50 mg. three times a day. In general, oral administration requires a higher dose than does intravenous administration. Usually, a small dosage is administered initially and the dosage is gradually increased until the optimal dosage for the host under treatment is determined.

The compounds of Formula I and their pharmaceutically acceptable salts may be formulated into conventional pharmaceutical compositions and administered by conventional modes of administration.

The compounds may be combined with pharmaceutically acceptable carriers and other conventional pharmaceutical adjuvants and administered orally in the form of tablets, dispersible powders, granules, capsules, elixirs, suspensions and the like or parenterally in the form of an injectable solution or suspension. The composition may be prepared by conventional means and may contain one or more conventional adjuvants such as sweetening agents (oral compositions only), other flavoring agents (oral compositions only), coloring agents (oral compositions only) and preserving agents.

Tablets may contain the active ingredient in admixture with conventional excipients, i.e., inert diluents such as calcium carbonate, sodium carbonate, lactose, talc and sodium citrate, granulating and disintegrating agents, e.g., starch, gum tragacanth, polyvinylpyrrolidone and alginic acid and also certain complex silicates, binding agents, e.g., starch, gelatin and acacia, and lubricating agents, e.g., magnesium stearate, stearic acid, talc and sodium lauryl sulfate. The tablets may be uncoated or coated by known techniques to delay disintegration and absorption in the gastrointestinal tract and thereby provide a sustained action over a longer period.

Capsules may contain a compound of Formula I, or a pharmaceutically acceptable acid addition salt thereof, alone or admixed with an inert solid diluent, e.g., calcium carbonate, calcium phosphate, kaolin, lactose and high molecular weight polyethylene glycols.

Suspensions, syrups and elixirs may contain a compound of Formula I, or a pharmaceutically acceptable acid addition salt thereof, in admixture with any of the conventional excipients utilized for the preparation of such compositions i.e., suspending agents, e.g., methylcellulose, tragacanth and sodium alginate, wetting agents, e.g., lecithin, polyoxyethylene stearate and polyoxyethylene sorbitan monooleate, preservatives, e.g., ethyl p-hydroxybenzoate, and diluents, e.g., ethanol, propylene glycol and glycerin.

Injectable compositions may contain salt and should, if necessary, be buffered to render them isotonic and be sterile.

The preferred pharmaceutical compositions from the stand-point of ease of preparation and administration are solid compositions, particularly tablets and hard-filled capsules.

A typical dosage unit may contain 25 to 1000, e.g., 75 to 1000, mg. of a compound of Formula I, or a pharmaceutically acceptable acid addition salt thereof.

Representative formulations prepared by conventional techniques for encapsulation in a hard gelatin capsule are:

| | |
|---|---|
| A. Compound of Formula I, e.g., | |
| the compound of Example 4 | 200 mg. |
| Lactose (spray-dried) | 160 mg. |
| Colloidal silica (Cab-O-Sil) | 6 mg. |
| Alginic acid | 60 mg. |
| B. Compound of Formula I, e.g., | |
| the compound of Example 13 | 150 mg. |
| Powdered lactose | 150 mg. |

Preferably, the active ingredient is micronized by conventional means and then mixed with the powdered lactose.

| | |
|---|---|
| C. Compound of Formula I, e.g., | |
| the compound of Example 14 | 200 mg. |
| Powdered lactose | 200 mg. |

Preferably the active ingredient is micronized by conventional means and then mixed with the powdered lactose.

| | |
|---|---|
| D. Compound of Formula I, e.g., | |
| the compound of Example 13 | 50 mg. |
| Powdered lactose | 150 mg. |
| Magnesium stearate | 2 mg. |

Preferably, the active ingredient is micronized by conventional means and then mixed with the powdered lactose.

A typical tablet may contain:

| | |
|---|---|
| A. Compound of Formula I, e.g., the | |
| compound of Example 3 | 100 mg. |
| Gum tragacanth | 10 mg. |
| Lactose (spray-dried) | 197.5 mg. |
| Corn starch | 25 mg. |
| Talc | 15 mg. |
| Magnesium stearate | 2.5 mg. |
| B. Compound of Formula I, e.g., the | |
| compound of Example 13 | 25 mg. |
| Polyvinylpyrrolidone (non-crosslinked; | |
| Povidone USP) | 3 mg. |
| Lactose (spray-dried) | 60 mg. |
| Corn starch | 10 mg. |
| Talc | 2.5 mg. |
| Magnesium stearate | 1 mg. |
| C. Compound of Formula I, e.g., the | |
| compound of Example 13 | 50 mg. |
| Polyvinylpyrrolidone (non-crosslinked; | |
| Povidone USP) | 6 mg. |
| Lactose (spray-dried) | 120 mg. |
| Corn starch | 20 mg. |
| Talc | 5 mg. |
| Magnesium stearate | 2 mg. |
| D. Compound of Formula I, e.g., the | |
| compound of Example 13 | 100 mg. |
| Powdered lactose | 100 mg. |

Preferably, the active ingredient is micronized by conventional means, mixed with the powdered lactose and tabletted by conventional means.

As is evident to those in the art, the compounds of Formula I may exist in two tautomeric forms, I(a) and I(b), while those wherein $R_2$ is hydrogen can also exist in a third tautomeric form, I(c),

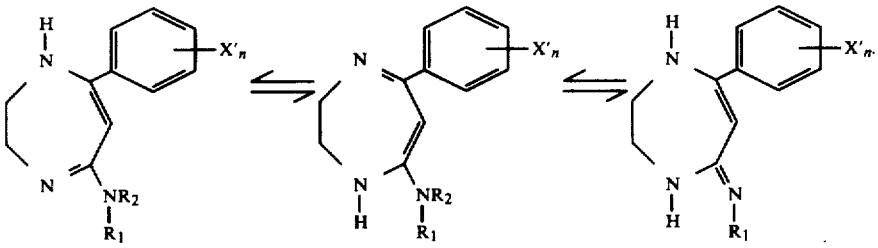

(I(a)) (I(b)) (I(c))

The possible tautomeric forms interconvert in the presence of acid. The principal form, Formula I(a), has been used exclusively throughout the specification and claims for simplicity. It should, however, be understood that Formula I is nothing more than a shorthand for Formulae I(a), I(b) and, if possible, I(c) and that Formula I embraces the tautomeric forms I(a), I(b) and, if possible, I(c). It goes without saying that all other formulae directed to the 1H-1,4-diazepines of this application (e.g., Formulae II–V, VII, VIII A, XIII–XVI, XVIII, XX–XXIV and XXVII–XXXV) also embrace their respective tautomeric forms, i.e., the corresponding formulae wherein the hydrogen atoms (protons) and double bonds ( || bonds) are as in Formulae I(b) and, if possible, I(c).

As is also evident to those in the art, the compounds of Formula VII may exist in numerous tautomeric forms, e.g., VII(a)–VII(d),

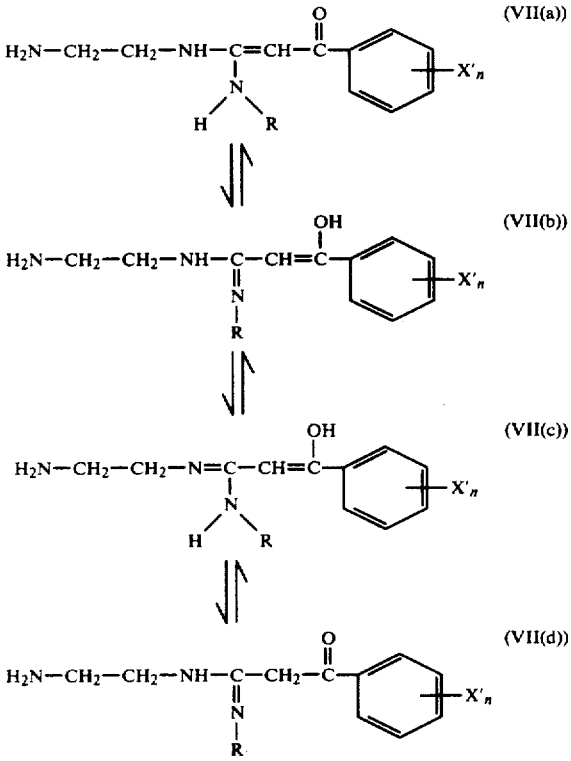

(VII(a)) (VII(b)) (VII(c)) (VII(d))

wherein the carbon-carbon double bonds can be cis or trans, i.e., wherein the —H and —NHR or the —H and —OH groups can be cis or trans to each other, and numerous hydrogen bonded forms thereof, all of which can interconvert. For simplicity, Formula VII(a) has been used exclusively throughout the specification since it is believed to be the thermodynamically most stable form, and the hydrogen bonds have been omitted. However, it should be understood that Formula VII is nothing more than a shorthand for Formulae VII(a)–VII(d), etc. and their cis-trans isomers and the hydrogen bonded forms thereof and that Formula VII embraces all possible tautomeric forms. It likewise goes without saying that Formulae VIIA, XI, XVII and XIX embrace their respective tautomeric forms, i.e., the formulae wherein the protons and || bonds are as in Formulae VII(b)–VII(d) and the isomeric and hydrogen bonded forms thereof.

The following examples show representative compounds encompassed by this invention and processes for their synthesis. However, it is to be understood that they are for purposes of illustration only.

EXAMPLE 1

β-(2-Aminoethylamino)-β-(1,1-dimethylethylamino)vinyl phenyl ketone

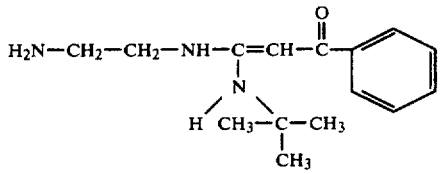

(XI)

(a) 50.0 ml. (750 mmol) of ethylenediamine were dissolved in 700 ml. of methylene chloride. 30.0 g (100 mmol) of 2-t-butyl-5-phenylisoxazolium perchlorate (J. Org. Chem. 31, 2039 (1966)) were added to the solution as a solid in small portions with stirring over a period of 20 minutes. The temperature of the reaction mixture was maintained at 20°–30° C. by cooling since the reaction is exothermic. Stirring was continued for one hour upon completion of the addition of the isoxazolium salt. The reaction mixture was diluted by addition of sufficient methylene chloride to bring the volume to 1 l. The reaction mixture was then extracted twice with 300 ml. portions of water and dried over anhydrous magnesium sulfate. The methylene chloride was stripped off at a reduced pressure to obtain an oil. The oil was dissolved in 300 ml. of anhydrous ether and filtered free of white solids. The white solids were washed with a small amount of anhydrous ether and the washings were combined with the filtrate. The combined filtrate and washings were evaporated at a reduced pressure to obtain the product as a colorless oil.

(b) 100 g. (330 mmol) of 2-t-butyl-5-phenylisoxazolium perchlorate were added portionwise to a solution of 150 ml. of ethylenediamine in 2 l. of methylene chloride stirred vigorously under nitrogen. The temperature of the reaction mixture was maintained at 20°-25° C. by varying the rate of addition of the isoxazolium salt and by cooling. Stirring was continued for one hour upon completion of the addition of the isoxazolium salt. The reaction mixture was extracted twice with 1 l. portions of water and dried over anhydrous magnesium sulfate. The methylene chloride was stripped off at reduced pressure, the resulting oil was dissolved in 1 l. of ether and the resulting solids (presumably a dimer (5.3 g.)) were removed by filtration. The ether was removed at reduced pressure to give the product as a thick pale yellow oil (80.6 g.).

(c) 602 g. (2.0 mol) of 2-t-butyl-5-phenylisoxazolium perchlorate were added portionwise to a mixture of 900 ml. of ethylenediamine and 12 l. of methylene chloride stirred vigorously at 20° C. under nitrogen over a period of about 1 hr. with external cooling so as to maintain a temperature of 20°-25° C. Stirring was continued for 2 hrs. subsequent to completion of the addition of the isoxazolium salt. The reaction mixture was extracted three times with 3 l. portions of water and once with 2 l. of saturated sodium chloride solution and was dried over anhydrous sodium sulfate. The methylene chloride was stripped off at 40° C. to obtain the crude product as a dark thick oil (498 g.).

EXAMPLE 2

β-(2-Aminoethylamino)-β-(1,1-dimethylethylamino)vinyl phenyl ketone.dihydrochloride (XII)

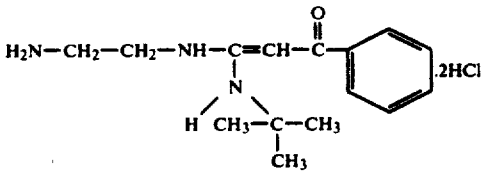

Addition of gaseous hydrogen chloride to a solution of the free base of Example 1(a) (Compound XI) yielded the product, m.p. 175° C. (decomp.)

N.M.R. ($CD_3$—SO—$CD_3$):

1.45 δ (9 proton singlet)
3.1 δ (2 proton multiplet)
3.6 δ (2 proton multiplet)
5.0 δ (2 proton singlet, both exchangeable)
7.6 δ (3 proton multiplet)
8.0 δ (2 proton multiplet)
8.6 δ (4 proton multiplet, all exchangeable)
9.7 δ (1 proton singlet, exchangeable)

EXAMPLE 3

5-t-Butylamino-7-phenyl-2,3-dihydro-1H-1,4-diazepine.perchlorate (XIII)

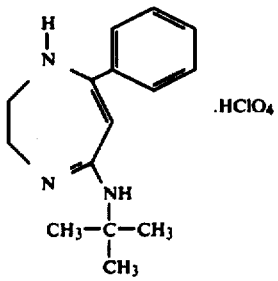

(a) 24.0 g. (92.0 mmol) of the product of Example 1(a) (Compound XI) were dissolved in 200 ml. of absolute ethanol. The solution was acidified to a pH of about 1 with 70% perchloric acid, refluxed under nitrogen for one hour and allowed to cool to room temperature. Addition of 500 ml. of anhydrous ether gave the product in the form of white crystals. Recrystallization from ethanol/ether gave white crystals, m.p. 169°-171° C. (decomp.)

N.M.R. ($CD_3$—SO—$CD_3$):

1.3 δ (9 proton singlet)
3.5 δ (4 proton multiplet)
4.8 δ (1 proton singlet)
7.4-8.2 δ (8 proton multiplet, 3 exchangeable)

I.R. (nujol): 3400, 3340, 1630, 1585, 1550, 1325, 1210, 1080 $cm^{-1}$

U.V. ($CH_3OH$):

$\lambda_{max.}=238$ ($\epsilon=14{,}900$)
$\lambda_{max.}=315$ ($\epsilon=22{,}100$)

$ED_{50}$ (Test (a)): 34.3 mg./kg.
$ED_{50}$ (Test (b)): 188 mg./kg.

(b) The process of Example 3(a) was repeated with the following modifications. The reaction mixture was acidified to a pH of 1 to 2 and the refluxing was halted after 40 minutes because the reaction mixture was turning green. The product was crystallized out in the form of off-white crystals by adding 500 ml. of anhydrous ether and cooling (17.7 g.). The mother liquor was evaporated down to a volume of 200 ml. at reduced pressure, allowed to reflux under nitrogen for 1½ hours and evaporated down to a volume of about 50 ml. at reduced pressure. 100 ml. of water were added to obtain additional product in the form of off-white crystals (6.2 g.). The two batches were combined and recrystallized from absolute ethanol/ether to obtain the product as white crystals (21.7 g.), m.p. 169°-171° C. (decomp.)

EXAMPLE 4

5-t-Butylamino-7-phenyl-2,3-dihydro-1H-1,4-diazepine, methane-sulfonate (XIV)

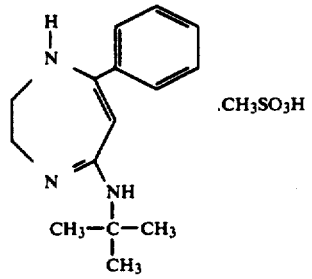

(a) 2.50 g (9.5 mmol) of the product of Example 1(a) or (b) (Compound XI) were dissolved in 50 ml. of absolute ethanol, 1.00 g (10.0 mmol) of methanesulfonic acid was added, and the resulting reaction mixture was refluxed for 20 minutes. The reaction mixture was allowed to cool and the ethanol was removed at reduced pressure to obtain an oil. Trituration of the oil with anhydrous ether gave the product as white crystals (3.0 g.). Recrystallization from isopropanol/ether gave white crystals (2.1 g), m.p. 159°-162° C.

N.M.R. ($CD_3$—SO—$CD_3$):

1.4 δ (9 proton singlet)
2.3 δ (3 proton singlet)
3.6 δ (4 proton multiplet)

5.0 δ (1 proton singlet)

7.4–8.4 δ (8 proton multiplet, 3 exchangeable)

(b) 498 g. (~1.91 mols) of the product of Example 1(c) (Compound XI) and 4.5 l. of absolute ethanol were stirred in a 12 l. flask at room temperature and 195 g. (2.03 mols) of methanesulfonic acid were added dropwise over a period of about 15 minutes such that the temperature rose to 35° C. The resulting reaction mixture was refluxed for 3 hrs. and allowed to cool to room temperature overnight. The ethanol was removed at reduced pressure and the thick oily residue was triturated with 3 l. of ethyl acetate and 1 l. of anhydrous ether until it crystallized. The crystalline material was filtered and washed well with anhydrous ether to give the crude product (562 g.), m.p. 145°–148° C.

EXAMPLE 5

5-t-Butylamino-7-(2'-chlorophenyl)-2,3-dihydro-1H-1,4-diazepine.hydrochloride

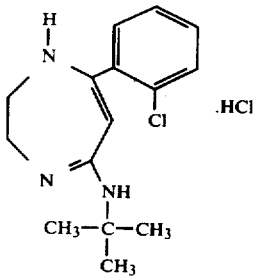

(XV)

Following the procedures of Examples 1 and 3(a) or , the product is obtained from ethylenediamine and -t-butyl-5-(2'-chlorophenyl)isoxazolium perchlorate using a solution of hydrogen chloride in ethanol for the yclization) as a crystalline solid, m.p. 152°–155° C. decomp.)

I.M.R. ($CD_3$—SO—$CD_3$):

1.35 δ (9 proton singlet)

3.6 δ (4 proton multiplet)

4.65 δ (1 proton singlet)

7.5 δ (4 proton multiplet)

8.45 δ (2 proton multiplet)

R. (nujol): 3200, 1620, 1550, 1320, 1275, 1240 $cm^{-1}$

.V. ($CH_3OH$):

$\lambda_{max.}=232$ ($\epsilon=6{,}200$)

$\lambda_{max.}=306$ ($\epsilon=17{,}000$)

est (a): −16% (mg./kg.)

he corresponding free base and other pharmaceutilly acceptable acid addition salts may be obtained nventionally.

EXAMPLE 6

5-t-Butylamino-7-(4'-methoxyphenyl)-2,3-dihydro-1H-1,4-diazepine.perchlorate

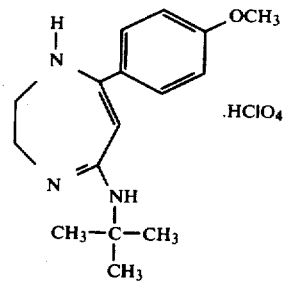

(XVI)

(a) Following the procedures of Examples 1 and 3(a) or 4, the product is obtained from ethylenediamine and 2-t-butyl-5-(4'-methoxyphenyl)isoxazolium perchlorate (using 70% perchloric acid for the cyclization) as a crystalline solid, m.p. 151°–152.5° C.

N.M.R. ($CD_3$—SO—$CD_3$):

1.3 δ (9 proton singlet)

3.5 δ (4 proton multiplet)

3.8 δ (3 proton singlet)

4.9 δ (1 proton singlet)

6.9 δ (7 proton multiplet, 8.3 δ 3 exchangeable)

I.R. (nujol): 3400, 3350, 1620, 1575, 1540, 1515, 1505, 1080 $cm^{-1}$

U.V. ($CH_3OH$):

$\lambda_{max}=214$ ($\epsilon=8{,}750$)

$\lambda_{max.}=258$ ($\epsilon=9{,}650$)

$\lambda_{max.}=318$ ($\epsilon=23{,}200$)

Test (a): −39% (80 mg./kg.)

(b) The uncyclized intermediate of Formula VII was synthesized from 6.64 g (20.0 mmol.) of 2-t-butyl-5-(4'-methoxyphenyl)isoxazolium perchlorate and 10 ml. (150 mmol.) of ethylenediamine by the process of Example 1(b). Cyclization was effected by dissolving the oil product in 100 ml. absolute ethanol, making the solution slightly acidic (pH of about 5) with a solution of hydrogen chloride in absolute ethanol and refluxing under nitrogen for 1½ hours. The ethanol was removed at reduced pressure to obtain a green oil which failed to yield crystals upon trituration. The oil was, therefore, dissolved in 150 ml. of water and neutralized with 2 N. sodium hydroxide. The free base was extracted with two 150 ml. portions of chloroform and the combined extracts were dried over anhydrous magnesium sulfate and evaporated down to an oil at reduced pressure. The product was obtained from isopropanol as light tan crystals by acidification with a solution of 70% perchloric acid in isopropanol (4.2 g.). Recrystallization from isopropanol gave the product in the form of off-white crystals (3.3 g.), m.p. 151°–152.5° C.

The corresponding free base and other pharmaceutically acceptable acid addition salts thereof may be obtained conventionally.

EXAMPLE 7

β-(2-Aminoethylamino)-β-(1,1-dimethylethylamino)vinyl 4-methylphenyl ketone

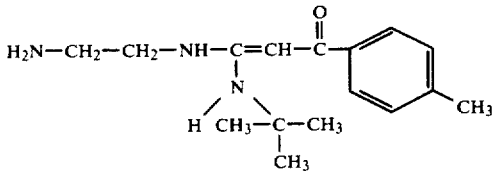

(XVII)

12 ml. (180 mmol) of ethylenediamine were dissolved in 400 ml. of methylene chloride. 8.0 g. (25 mmol) of 2-t-butyl-5-(4'-methylphenyl)isoxazolium perchlorate were added portionwise to the resulting solution while stirring over a 15 minute period so as to maintain the temperature of the reaction mixture at 20°-25° C. under nitrogen. Stirring was continued for 30 minutes upon completion of the addition of the isoxazolium salt. The reaction mixture was then extracted twice with 400 ml. portions of water and dried over anhydrous magnesium sulfate. The methylene chloride was evaporated at reduced pressure to obtain the product as a light yellow oil.

EXAMPLE 8

5-t-Butylamino-7-(4'-methylphenyl)-2,3-dihydro-1H-1,4-diazepine.methanesulfonate

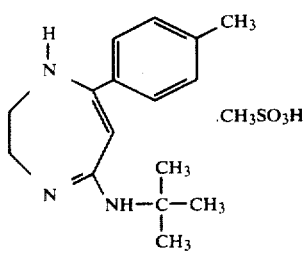

(XVIII)

The entire yield (25 mmol?) of Example 7 (Compound XVII) was dissolved in 150 ml. of absolute ethanol, 2.45 g. (25 mmol) of methanesulfonic acid were added to the solution and the reaction mixture was allowed to reflux under nitrogen for 20 minutes. The ethanol was evaporated off at reduced pressure and the product was crystallized from isopropanol/ether in the form of off-white crystals (8.7 g.). Recrystallization from isopropanol/ether gave the product as white crystals (7.7 g.), m.p. 174°-177° C. (decomp.)

N.M.R. ($CDCl_3$):

1.4 δ (9 proton singlet)
2.3 δ (3 proton broad singlet)
2.3 δ (3 proton singlet)
3.3-3.8 δ (4 proton multiplet)
4.9 δ (1 proton broad singlet)
7.0-8.4 δ (7 proton multiplet, 3 exchangeable)

I.R. ($CHCl_3$): 3460, 3320, 3180, 3020, 1620, 1550, 1490, 1450, 1380, 1340, 1180, 1055 $cm^{-1}$

U.V. ($CH_3OH$):

$\lambda_{max.}$ = 243 mμ (ε = 15,300)
$\lambda_{max.}$ = 318 mμ (ε = 23,400)

$ED_{50}$ (Test (a)): 15.0 mg./kg.
Test (b): −17% (200 mg./kg.)
$ED_{25}$ (Test (c)): 158.5 mg./kg.
Test (d): −20% (200 mg./kg.; 6 hrs.)

The corresponding free base and other pharmaceutically acceptable acid addition salts thereof may be obtained conventionally.

EXAMPLE 9

β-(2-Aminoethylamino)-β-(1,1-dimethylethylamino)vinyl 3,4-dimethylphenyl ketone

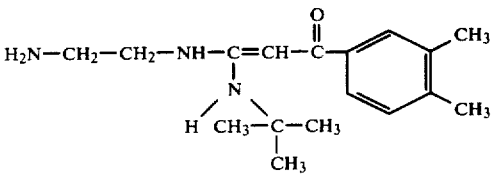

(XIX)

The product (6.6 g.) was obtained as a thick pale yellow oil from 12 ml. (180 mmol.) of ethylenediamine and 7.6 g. (23.0 mmol.) of 2-t-butyl-5-(3',4'-dimethylphenyl)isoxazolium perchlorate by a process substantially identical to that of Example 7.

EXAMPLE 10

5-t-Butylamino-7-(3',4'-dimethylphenyl)-2,3-dihydro-1H-1,4-diazepine.methanesulfonate

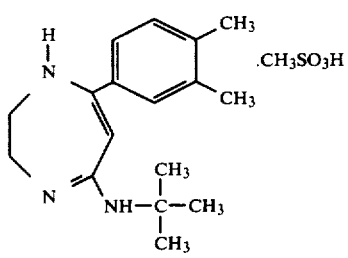

(XX)

The crude product (8.1 g.) was obtained as a light green solid from 6.6 g. (22.8 mmol.) of the crude product of Example 9 (Compound XIX) and 2.24 g. (27.8 mmol.) of 98% methanesulfonic acid by a process substantially identical to that of Example 8. Recrystallization from isopropanol/ether gave the product as white crystals (6.6 g.), m.p. 200°-202° C. (decomp.)

N.M.R. ($CDCl_3$):

1.4 δ (9 proton singlet)
2.25 δ (6 proton broad singlet)
2.6 δ (3 proton singlet)
3.2-3.8 δ (4 proton multiplet)
4.9 δ (1 proton broad singlet)
7.0-7.5 δ (4 proton multiplet, 1 exchangeable)
7.6-8.5 δ (2 proton multiplet, both exchangeable)

I.R. ($CHCl_3$): 3430, 3280, 3150, 2990, 1625, 1550, 1490, 1450, 1405, 1375, 1335, 1235, 1175, 1045 $cm^{-1}$

U.V. ($CH_3OH$):

$\lambda_{max.}$ = 245 mμ (ε = 12,300)
$\lambda_{max.}$ = 319 mμ (ε = 21,400)

Test (a): −43% (80 mg./kg.)
$ED_{25}$ (Test (b)): 185 mg./kg.
Test (c): −28% (100 mg./kg.)

The corresponding free base and other pharmaceutically acceptable acid addition salts thereof may be obtained conventionally.

EXAMPLE 11

5-Methylamino-7-phenyl-2,3-dihydro-1H-1,4-diazepine.perchlorate (XXI)

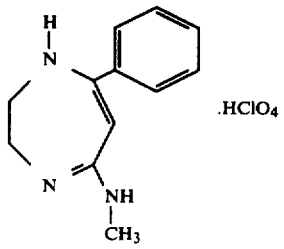

Following the procedure of Examples 1 and 3(a) or 4, the product is obtained from ethylenediamine and 2-methyl-5-phenylisoxazolium perchlorate (using 70% perchloric acid for the cyclization).

EXAMPLE 12

5-Ethylamino-7-phenyl-2,3-dihydro-1H-1,4-diazepine.methanesulfonate (XXII)

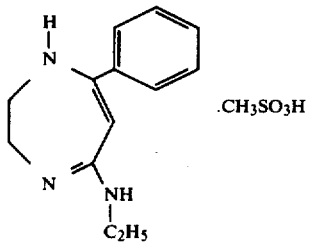

Following the procedure of Examples 1 and 3(a) or 4, the product is obtained from ethylenediamine and 2-ethyl-5-phenylisoxazolium perchlorate (using methanesulfonic acid for the cyclization).

EXAMPLE 13

5-Amino-7-phenyl-2,3-dihydro-1H-1,4-diazepine.methanesulfonate (XXIII)

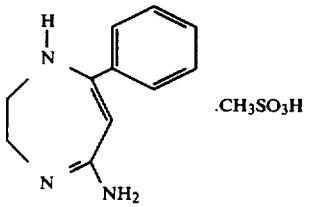

(a) 2.00 g. of crude 5-t-butylamino-7-phenyl-2,3-dihydro-1H-1,4-diazepine.methanesulfonate (Compound XIV) were heated in an oil bath at 160°-165° C. for a period of 15 minutes. When the melt ceased to bubble, sufficient isopropanol was added to the hot melt to form a solution. Addition of dry ether gave the product in the form of white crystals (1.6 g.), m.p. 176°-177.5° C.

| $C_{11}H_{13}N_3.CH_3SO_3H$ | Analysis | C | H | N | O | S |
|---|---|---|---|---|---|---|
| | Calculated | 50.9 | 6.1 | 14.8 | 16.9 | 11.3 |
| | Found | 50.9 | 6.4 | 14.3 | — | 11.3 |

N.M.R. ($CD_3SOCD_3$):
2.3 δ (3 proton singlet)
3.2-3.8 δ (4 proton multiplet)
4.85 δ (1 proton broad singlet)
7.2-7.85 δ (7 proton multiplet, 2 exchangeable)
8.2-8.8 δ (2 proton multiplet, both exchangeable)

I.R. (nujol): 3400, 3310, 3190, 1650, 1590, 1580, 1230, 1180, 1165, 1110 $cm^{-1}$ U.V. ($CH_3OH$):
$\lambda_{max.}=237$ mμ ($\epsilon=15{,}100$)
$\lambda_{max.}=313$ mμ ($\epsilon=18{,}600$)

Thin layer chromatography points to the presence of two tautomeric forms.

(b) The product was also produced from pure starting material by the same process except that 2 drops of methanesulfonic acid were added to the reaction mixture to catalyze the reaction.

(c) 100 g. of crude 5-t-butylamino-7-phenyl-2,3-dihydro-1H-1,4-diazepine.methanesulfonate (Compound XIV; from Example 4(b)) were heated under nitrogen at 160° C. in an oil bath with stirring. The starting material melted and began to bubble. When the melt ceased to bubble, 200 ml. of isopropanol were slowly added with stirring. After 15 minutes, the obtained solid material was filtered and washed with petroleum ether to obtain the product (68 g.), m.p. 175°-177° C. Concentration of the mother liquor and crystallization from isopropanol gave additional product (13 g.), m.p. 174°-176° C. Recrystallization raised the melting point to 176°-177° C.

(d) The process was repeated using 600 g. of crude 5-t-butylamino-7-phenyl-2,3-dihydro-1H-1,4-diazepine.methanesulfonate to obtain 468 g. of product, m.p. 175°-177° C.

$ED_{50}$ (Test (a)): 13.8 mg./kg.
$ED_{25}$ (Test (b)): 17.3 mg./kg.
Test (d):
−29% (200 mg./kg.; 2 hrs.)
−17% (25 mg./kg.; 4 hrs.)
−23% (50 mg./kg.; 4 hrs.)
−26% (100 mg./kg.; 4 hrs.)
−58% (200 mg./kg.; 4 hrs.)
−48% (200 mg./kg.; 6 hrs.)

Upon administration to mammals, e.g., normal fasting Macaca irus and Cebus monkeys at an oral dosage of 7.5 mg./kg. body weight, marked hypoglycemia results.

The corresponding free base and other pharmaceutically acceptable acid addition salts thereof may be obtained conventionally.

EXAMPLE 14

5-Amino-7-(4'-methylphenyl)-2,3-dihydro-1H-1,4-diazepine.methanesulfonate (XXIV)

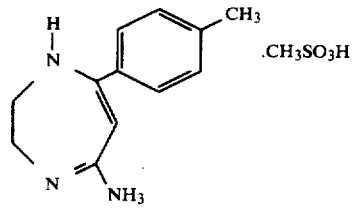

1.9 g. of the product of Example 8 (Compound XVIII) was heated in an oil bath at a temperature of 200° C. for 30 minutes with one drop of methanesulfonic acid. When the melt ceased to bubble, 10 ml. of isopropanol were added to form a solution. The solution was allowed to cool and anhydrous ether was added to obtain the crystalline product (1.6 g.), m.p. 200°-210° C.

N.M.R. ($CD_3SOCD_3$):

2.36 δ (3 proton singlet)
2.43 δ (3 proton singlet)
3.50 δ (4 proton multiplet)
4.90 δ (1 proton singlet)
7.40 δ (6 proton multiplet, 2 exchangeable)
8.50 δ (2 proton broad doublet, both exchangeable)

I.R. (nujol): 3300, 3195, 1660, 1635, 1570, 1535, 1210, 1170, 1050 $cm^{-1}$

U.V. ($CH_3OH$):

$\lambda_{max.}=244$ mμ ($\epsilon=12,150$)
$\lambda_{max.}=314$ mμ ($\epsilon=16,900$)

$ED_{50}$ (Test (a)): 19.3 mg./kg.

The corresponding free base and other pharmaceutically acceptable acid addition salts thereof may be obtained conventionally.

EXAMPLE 15

7-Phenyl-1,2,3,4-tetrahydro-1,4-diazepine-5-one (XXV)

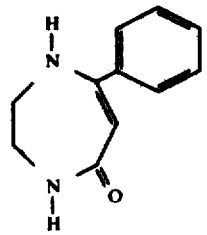

[15.5 g. (59.5 mmol.) of the product of Example 1(a) or 1(b) (Compound XI) were dissolved in 100 ml. of xylene and allowed to reflux under nitrogen for 3 hours. (After 30 minutes crystals began to form.) The reaction mixture was allowed to cool to room temperature overnight. The crystals that formed were isolated by filtration, washed with xylene and dried to obtain the product as white crystals (8.5 g.), m.p. 204°-206° C. (turns dark).] Lit: Ried et al., Chem. Ber. 87, 1811-1814 (1954), m.p. 209°-210° C.; Hofmann et al., J. Org. Chem. 27, 3565-3568 (1962), m.p. 206°-209° C.

[N.M.R. ($CD_3$—SO—$CD_3$):

3.2-3.8 δ (4 proton multiplet)
5.3 δ (1 proton singlet)
7.2-8.0 δ (6 proton multiplet, 1 exchangeable)
9.5 δ (1 proton broad band)

I.R. (nujol): 3200, 1610, 1585, 1550 $cm^{-1}$

U.V. ($CH_3OH$):

$\lambda_{max.}=235$ mμ ($\epsilon=12,500$)
$\lambda_{max.}=319$ mμ ($\epsilon=22,200$)]

EXAMPLE 16

5-Ethoxy-7-phenyl-2,3-dihydro-1H-1,4-diazepine.tetrafluoroborate (XXVI)

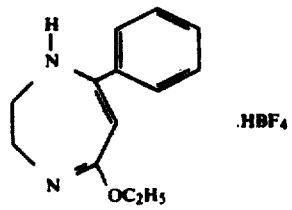

[10.0 g. (53.0 mmol.) of 7-phenyl-1,2,3,4-tetrahydro-1,4-diazepine-5-one (Compound XXV) were suspended in 100 ml. of dry methylene chloride under nitrogen and stirred. 10.1 g. (53.0 mmol.) of triethyloxonium tetrafluoroborate were added portionwise to the stirred suspension over a 20 minute period to maintain the reaction mixture at a temperature of 20°-25° C., the reaction being slightly exothermic. After the addition was completed, the reaction mixture was stirred for an additional 30 minutes at room temperature. The solvent was evaporated off to obtain 16.6 g. of oily crystals. The solids were triturated with ethyl acetate to give the product in the form of white crystals (8.0 g.), m.p. 150°-155° C. Recrystallization from chloroform raised the melting point to 157.5°-158.5° C.]

[N.M.R. ($CD_3SOCD_3$):

1.2 δ (3 proton triplet)
3.9 δ (4 proton singlet)
4.1 δ (2 proton quartet)
5.55 δ (1 proton singlet)
7.55 δ (5 proton singlet)
9.2 δ (2 protons, both exchangeable)

I.R. (nujol): 3450, 3360, 1635, 1605 $cm^{-1}$

U.V. ($CH_3OH$):

$\lambda_{max.}=220$ mμ ($\epsilon=5,250$)
$\lambda_{max.}=275$ mμ ($\epsilon=23,800$)]

*The compound is produced by the portionwise addition (so as to maintain the reaction mixture at a temperature of 20°-25° C.) of 10.1 g.(53.0 mmol.) of triethyloxonium tetrafluoroborate to a suspension of 10.0 g. (53.0 mmol.) of 7-phenyl-1,2,3,4-tetrahydro-1,4-diazepine-5-one (Compound XXV) in 100 ml. of dry methylene chloride stirred under nitrogen followed by stirring for an additional 30 minutes at room temperature.*

EXAMPLE 17

5-Methylamino-7-phenyl-2,3-dihydro-1H-1,4-diazepine.tetrafluoroborate (XXVII)

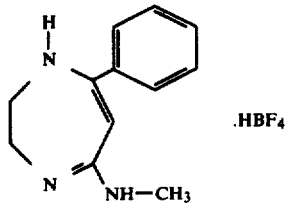

[3.20 g. of 5-ethoxy-7-phenyl-2,3-dihydro-1H-1,4-diazepine.tetrafluoroborate (Compound XXVI) and 15-20 ml. of methylamine were placed in a reaction bomb and allowed to stand for 1½ hours. To complete the reaction, the reaction mixture was heated at 40°-50° C. for 1½ hours. The excess methylamine was allowed to evaporate off, the resulting oil was dissolved in chloroform, and the chloroform was stripped off at reduced pressure to obtain an oil. Crystallization of the oil from isopropanol/ether yielded the product as white crystals (2.9 g.), m.p. 119°-122° C. The product was dissolved in 5% methanol/chloroform and the resulting solution was filtered through 3-5 ml. of silica gel and evaporated to dryness. Crystallization of the residue from isopropanol/ether gave the product (2.8 g.), m.p. 121.5°-123° C.]

[N.M.R. ($CD_3SOCD_3$):

2.8 δ (3 proton doublet, singlet after exchange with $D_2O$)
3.45 δ (4 proton singlet)

4.7 δ (1 proton singlet)
7.0–8.0 δ (8 protons, 3 exchangeable)
I.R. (nujol): 3380, 1595, 1545, 1310 $cm^{-1}$
U.V. ($CH_3OH$):
$\lambda_{max.}$ = 233 mμ (δ = 13,600)
$\lambda_{max.}$ = 297 mμ (ε = 26,300)
Test (a): −27% (80 mg./kg.)]

*The compound is obtained by reacting 3.20 g. of 5-ethoxy-7-phenyl-2,3-dihydro-1H-1,4-diazepine.tetrafluoroborate and 15–20 ml. of methylamine in a reaction bomb for 1½ hours followed by heating at 40°–50° C. for 1¼ hours after which the excess methylamine is allowed to evaporate off.*

The corresponding free base and other pharmaceutically acceptable acid addition salts may be obtained conventionally.

EXAMPLE 18

5-n-Butylamino-7-phenyl-2,3-dihydro-1H-1,4-diazepine.perchlorate (XXVIII)

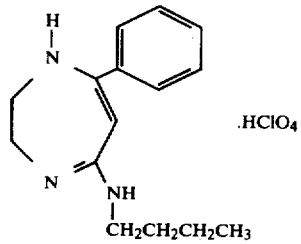

The product [was] *is* obtained from 2.00 g. (6.58 mmol.) of Compound XXVI and 10.0 ml. of n-butylamine by refluxing under nitrogen for 5 minutes, evaporating off the excess n-butylamine at reduced pressure, dissolving the resulting oil in 50 ml. of chloroform, washing the chloroform solution with 50 ml. of water, treating the chloroform solution with 50 ml. of cold 2 N. sodium hydroxide to liberate the free base, drying the chloroform solution over anhydrous magnesium sulfate, acidifying the chloroform solution with a solution of 70% perchloric acid in isopropanol, and evaporating off the solvent. [The oily product crystallized upon trituration with water (1.8 g.). Crystallization from isopropanol gave white crystals (Compound XXV) (0.40 g.), m.p. 141°–151° C. Evaporation of the mother liquor to an oil and trituration with ether and cooling gave the product as white crystals (1.2 g.), m.p. 59°–64° C.]

[N.M.R. ($CDCl_3$):
0.7–1.9 δ (7 proton multiplet)
3.0–3.8 δ (6 proton multiplet)
5.15 δ (1 proton singlet)
5.45 δ (1 proton broad peak, exchangeable)
5.95 δ (2 protons, both exchangeable)
7.2–7.7 δ (5 proton multiplet)
I.R. (KBr): 3230, 1590, 1535, 1110 $cm^{-1}$
U.V. ($CH_3OH$):
$\lambda_{max.}$ = 235 mμ (ε = 13,300)
$\lambda_{max.}$ = 298 mμ (ε = 26,200)
Test (a): −17% (40 mg./kg.)]

The corresponding free base and other pharmaceutically acceptable acid addition salts thereof may be obtained conventionally.

EXAMPLE 19

5-Dimethylamino-7-phenyl-2,3-dihydro-1H-1,4-diazepine.tetrafluoroborate (XXIX)

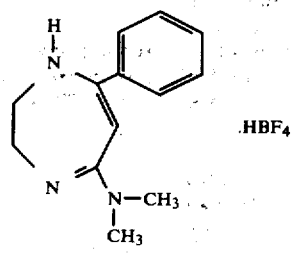

[3.50 g. (11.5 mmol.) of 5-ethoxy-7-phenyl-2,3-dihydro-1H-1,4-diazepine.tetrafluoroborate (Compound XXVI) and 10–15 ml. of dimethylamine were placed in a reaction bomb and heated at 100° C. for 20 minutes. The excess dimethylamine was allowed to evaporate off and the residue was dissolved in chloroform. The chloroform solution was filtered and evaporated at reduced pressure to obtain an oil. The oil was crystallized from isopropanol/ether to obtain the product as off-white crystals (3.2 g.), m.p. 125°–127° C. The product was dissolved in chloroform, evaporated at reduced pressure to an oil and recrystallized from isopropanol/ether to obtain white crystals (3.0 g.), m.p. 126.5°–128.5° C.]

[N.M.R. ($CD_3SOCD_3$):
2.85 δ (6 proton singlet)
3.45 δ (4 proton singlet)
4.9 δ (1 proton singlet)
6.0–7.4 δ (2 proton peak, both exchangeable)
7.1–7.7 δ (5 proton multiplet)
I.R. ($CHCl_3$): 3480, 3380, 1490, 1530, 1420, 1375, 1335, 1305 $cm^{-1}$
U.V. ($CH_3OH$):
$\lambda_{max.}$ = 243 mμ (ε = 9,500)
$\lambda_{max.}$ = 304 mμ (ε = 33,400)]

*The product is obtained by heating 3.50 g. (11.5 mmol.) of 5-ethoxy-7-phenyl-2,3-dihydro-1H-1,4-diazepine.tetrafluoroborate and 10–15 ml. of dimethylamine in a reaction bomb at 100° C. for 20 minutes after which the excess dimethylamine is allowed to evaporate off.*

The corresponding free base and other pharmaceutically acceptable acid addition salts thereof may be obtained conventionally.

EXAMPLE 20

5-Pyrrolidino-7-phenyl-2,3-dihydro-1H-1,4-diazepine.-tetrafluoroborate (XXX)

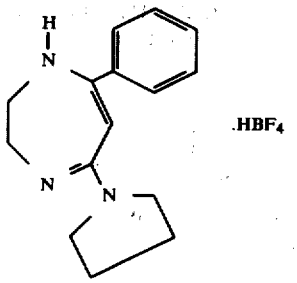

[3.8 g. (12.5 mmol.) of Compound XXVI were dissolved in 10.0 ml. of pyrrolidine and heated to reflux for 10 minutes under nitrogen. The excess pyrrolidine was then evaporated off and the resulting oil was dissolved in about 10 ml. of isopropanol. Crystallization commenced. About 20 ml. of dry ether were slowly added to obtain the product as off-white crystals (3.8 g.). Recrystallization from isopropanol yielded the product as white crystals (3.5 g.), m.p. 139.5°-140.5° C.]

[N.M.R. ($CDCl_3$):

1.6-2.4 δ (4 proton multiplet)
2.8-3.8 δ (8 proton multiplet)
5.1 δ (1 proton singlet)
5.6 δ (2 proton broad band, both exchangeable)
7.1-7.8 δ (5 proton multiplet)

I.R. ($CHCl_3$): 3480, 3380, 1590, 1520, 1455, 1350, 1330, 1305, 1080 $cm^{-1}$

U.V. ($CH_3OH$):

$\lambda_{max.}=240$ mμ ($\epsilon=5{,}750$)
$\lambda_{max.}=308$ mμ ($\epsilon=25{,}900$)

Test (a): −34% (80 mg./kg.)]

*The compound is obtained by heating 3.8 g. (12.5 mmol.) of Compound XXVI dissolved in 10.0 ml. of pyrrolidine to reflux for 10 minutes under nitrogen followed by evaporation of the excess pyrrolidine.*

The corresponding free base and other pharmaceutically acceptable acid addition salts may be obtained conventionally.

EXAMPLE 21

5-(N'-2-hydroxyethylpiperazino)-7-phenyl-2,3-dihydro-1H-1,4-diazepine.tetrafluoroborate (XXXI)

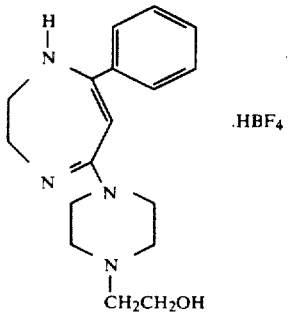

[3.1 g. (10.2 mmol.) of Compound XXVI and 2.1 g. of freshly distilled N-2-hydroxyethylpiperazine were combined and heated at 100° C. for 1 hour. After cooling, the product was chromatographed on 100 ml. of silica gel using gradient elution with methanol/-chloroform mixtures. The fraction containing the product was recrystallized from isopropanol (2.05 g.), m.p. 120°-121.5° C.]

[N.M.R. ($D_2O$):

2.42 δ (6 proton multiplet)
3.32 δ (10 proton broad multiplet)
4.95 δ (1 proton broad singlet)
7.34 δ (5 proton multiplet)

I.R. ($CHCl_3$): 3500-3300, 3100-2840, 1595, 1525, 1450, 1368, 1340, 1310, 1270-1203, 1075, 1020, 947, 895 $cm^{-1}$

U.V. ($CH_3OH$):

$\lambda_{max.}=243$ mμ ($\epsilon=10{,}470$)
$\lambda_{max.}=309$ mμ ($\epsilon=26{,}200$)

Test (a): −25% (80 mg./kg.)]

*The product is obtained by heating 3.1 g. (10.2 mmol.) of Compound XXVI and 2.1 g. of freshly distilled N-2-hydroxyethylpiperazine at 100° C. for 1 hour.*

The corresponding free base and other pharmaceutically acceptable acid addition salts thereof may be obtained conventionally.

EXAMPLE 22

5-Hydrazino-7-phenyl-2,3-dihydro-1H-1,4-diazepine.methanesulfonate (XXXII)

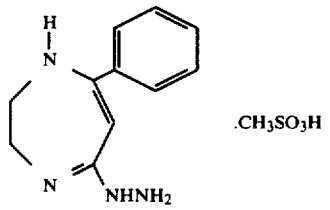

5.0 g. of 5-t-butylamino-7-phenyl-2,3-dihydro-1H-1,4-diazepine.methanesulfonate (Compound XIV) were allowed to reflux in 25 ml. of anhydrous hydrazine under nitrogen for 30 minutes. The excess hydrazine was stripped off at reduced pressure. To the resulting oil 50 ml. of isopropanol followed by 50 ml. of anhydrous ether were added to obtain white crystals. The crystals (1.8 g.), m.p. 139.5°-141.5° C., were washed with 1:1 isopropanol/ether and the washing was combined with the mother liquor. The combined mother liquor-washing was evaporated at reduced pressure to obtain an oil (4.0 g.). The oil was chromatographed on 125 ml. of silica gel using chloroform, 2% methanol in chloroform, 10% methanol in chloroform and 50% methanol in chloroform as the eluants. The 50% methanol in chloroform eluate was evaporated at reduced pressure to obtain an oil (1.3 g.) which crystallized upon trituration with anhydrous ether (1.0 g.), m.p. 85°-88.5° C.

N.M.R. ($CDCl_3$):

2.6-3.4 δ (4 proton multiplet)
4.8 δ (4 protons broad adsorption, all exchangeable)
5.8 δ (1 proton singlet)
7.0-7.8 δ (5 proton multiplet)

The obtained 5-hydrazino-7-phenyl-2,3-dihydro-1H-1,4-diazepine was converted into its methanesulfonate salt by addition of a solution of 0.5 g. of methanesulfonic acid in 10 ml. of isopropanol to a solution of about 1.3 g. of the crude free base in 25 ml. of isopropanol with cooling. After a few minutes, off-white crystals formed and 50 ml. of anhydrous ether were added. The crystals were filtered, washed with ether and dried to obtain 1.6 g. of product, m.p. 187°-190° C. Recrystallization from absolute ethanol/ether gave the product in the form of white crystals (1.4 g.), m.p. 190.5°-191.5° C. Test (a): −57% (80 mg./kg.)

Other pharmaceutically acceptable acid addition salts may be similarly obtained.

EXAMPLE 23

5-t-Butylamino-7-phenyl-2,3-dihydro-1H-1,4-diazepine (XXXIII)

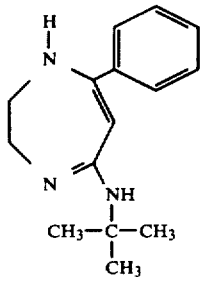

10.0 g. (29.5 mmol) of the methanesulfonate salt of Example 4 (Compound XIV) were dissolved in 50 ml. of water, the solution was cooled in an ice bath and 50 ml. of 2 N. sodium hydroxide were added. The aqueous solution was extracted twice with 150 ml. portions of chloroform, and the chloroform extracts were combined and dried over anhydrous magnesium sulfate. Removal of the chloroform at reduced pressure yielded an oil. Upon addition of 50 ml. of anhydrous ether, most of the oil dissolved leaving some off-white solids (1.0 g) which were removed by filtration. The filtrate was evaporated down to a minimum volume under reduced pressure. Slow addition of heptane and cooling yielded the product as white crystals (3.0 g.), m.p. 102°-103.5° C. A second crop (2.0 g.), m.p. 93°-97° C., was also obtained.

N.M.R. ($CD_3$-SO-$CD_3$):

1.3 δ (9 proton singlet)

3.6 δ (4 proton multiplet)

4.65 δ (1 proton singlet)

7.3 δ (7 proton multiplet, 2 exchangeable)

I.R. (nujol): 1620, 1580, 1315, 1260 and 1240 $cm^{-1}$

U.V. ($CH_3OH$):

$\lambda_{max.}=234$ ($\epsilon=13{,}200$)

$\lambda_{max.}=318$ ($\epsilon=19{,}300$)

Other corresponding pharmaceutically acceptable acid addition salts may be prepared conventionally.

EXAMPLE 24

5-Amino-7-phenyl-2,3-dihydro-1H-1,4-diazepine (XXXIV)

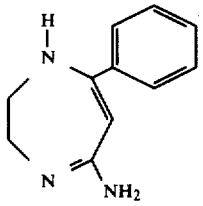

The product is produced from the corresponding methanesulfonate salt (Compound XXIII) by the process of Example 23.

EXAMPLE 25

5-Amino-7-(3',4'-dimethylphenyl)-2,3-dihydro-1H-1,4-diazepine.methanesulfonate (XXXV)

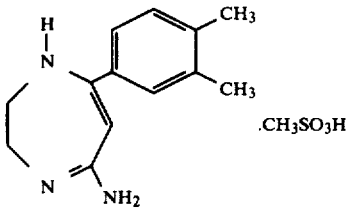

The product was obtained from the product of Example 10 following the procedure of Example 14, except that the oil bath was at 210° C., m.p. 180°-181.5° C. $ED_{50}$(Test (a)): 66.6 mg./kg.

The corresponding free base and other pharmaceutically acceptable acid addition salts thereof may be obtained conventionally.

All N.M.R. spectra were taken at ambient temperature on a 60 mHz N.M.R. spectrometer and all chemical shifts are given in p.p.m. (δ) relative to tetramethylsilane. Where a single δ value is given for anything other than a singlet, it is its center point. All U.V. data are given in mμ.

What is claimed is:

1. A compound of the formula

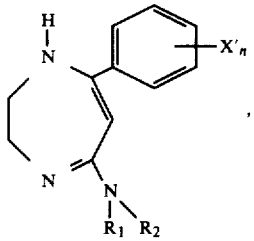

wherein $R_1$ is hydrogen, alkyl of 1 to 6 carbon atoms or amino, $R_2$ is hydrogen or alkyl of 1 to 6 carbon atoms, with the provisos that (1) at least one of $R_1$ and $R_2$ is not a tertiary alkyl group and (2) $R_2$ is hydrogen when $R_1$ is amino, each X' is independently alkyl of 1 to 4 carbon atoms, alkoxy of 1 to 4 carbon atoms or halo, or two X's on adjacent carbon atoms together are methylenedioxy, and n is 0, 1, 2 or 3, or a pharmaceutically acceptable acid addition salt thereof.

2. A pharmaceutically acceptable acid addition salt of a compound according to claim 1.

3. A compound according to claim 1 having the formula

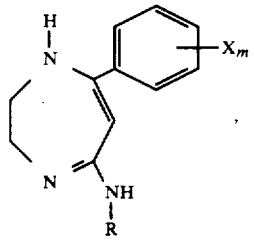

wherein R is alkyl of 1 to 6 carbon atoms, each X is independently alkyl of 1 to 4 carbon atoms, alkoxy of 1 to 4 carbon atoms or halo, and m is 0, 1 or 2, or a pharmaceutically acceptable acid addition salt thereof.

4. A compound according to claim 3 having the formula

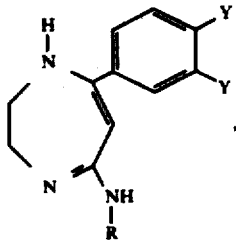

wherein R is alkyl of 1 to 6 carbon atoms, and each Y is hydrogen, alkyl of 1 to 3 carbon atoms, methoxy, ethoxy, chloro or bromo, with the proviso that at least one Y is hydrogen, or a pharmaceutically acceptable acid addition salt thereof.

5. A compound according to claim 4 wherein each Y is hydrogen, or a pharmaceutically acceptable acid addition salt thereof.

6. A compound according to claim 1 wherein each X' is independently alkyl of 1 to 3 carbon atoms, methoxy, ethoxy, chloro or bromo, and n is 0, 1 or 2, or a pharmaceutically acceptable acid addition salt thereof.

7. A compound according to claim 6 having the formula

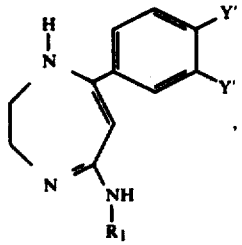

wherein $R_1$ is hydrogen, alkyl of 1 to 6 carbon atoms or amino, and each Y' is independently hydrogen, methyl, ethyl, methoxy or ethoxy, or a pharmaceutically acceptable acid addition salt thereof.

8. A compound according to claim 7 wherein each Y' is independently hydrogen, methyl or methoxy, or a pharmaceutically acceptable acid addition salt thereof.

9. A compound according to claim 7 wherein $R_1$ is hydrogen or t-butyl, or a pharmaceutically acceptable acid addition salt thereof.

10. A compound according to claim 9 wherein each Y' is independently hydrogen, methyl or methoxy, or a pharmaceutically acceptable acid addition salt thereof.

11. A compound according to claim 10 having the formula

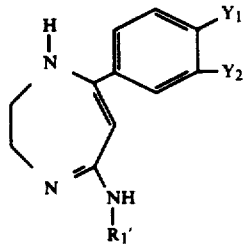

wherein $R_1'$ is hydrogen or t-butyl, $Y_1$ is hydrogen, methyl or methoxy, and $Y_2$ is hydrogen or methyl, or a pharmaceutically acceptable acid addition salt thereof.

12. A pharmaceutically acceptable acid addition salt of a compound according to claim 11.

13. A compound according to claim 11 wherein $R_1'$ is hydrogen, or a pharmaceutically acceptable acid addition salt thereof.

14. A pharmaceutically acceptable acid addition salt of a compound according to claim 13.

15. The compound according to claim 13 having the formula

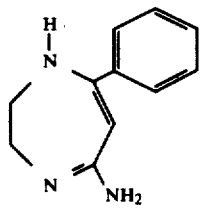

or a pharmaceutically acceptable acid addition salt thereof.

16. The compound according to claim 15 having the formula

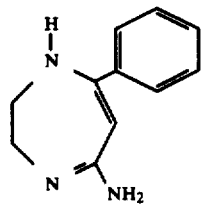

17. A pharmaceutical acceptable acid addition salt according to claim 15 of the compound of the formula

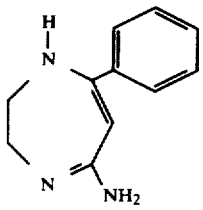

18. The pharmaceutically acceptable acid addition salt according to claim 17 having the formula

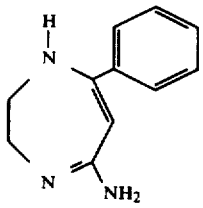

.$CH_3SO_3H$.

19. The compound according to claim 11 having the formula

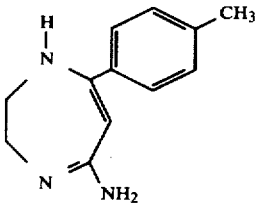

or a pharmaceutically acceptable acid addition salt thereof.

20. The pharmaceutically acceptable acid addition salt according to claim 19 having the formula

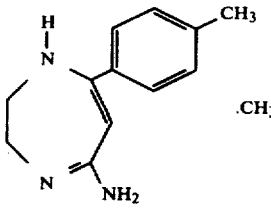

.$CH_3SO_3H$.

21. The compound according to claim 11 having the formula

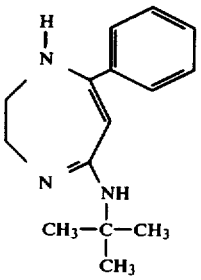

or a pharmaceutically acceptable acid addition salt thereof.

22. The compound according to claim 21 having the formula

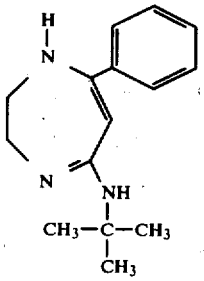

23. A pharmaceutically acceptable acid addition salt according to claim 21 of the compound of the formula

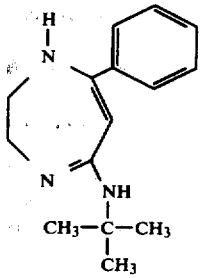

24. The pharmaceutically acceptable acid addition salt according to claim 23 having the formula

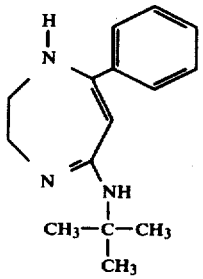

.$HClO_4$.

25. The pharmaceutically acceptable acid addition salt according to claim 23 having the formula

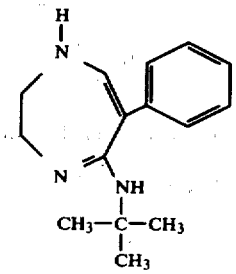

.$CH_3SO_3H$.

26. The compound according to claim 11 having the formula

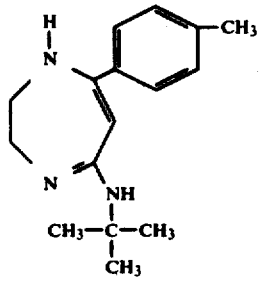

or a pharmaceutically acceptable acid addition salt thereof.

27. The pharmaceutically acceptable acid addition salt according to claim 26 having the formula

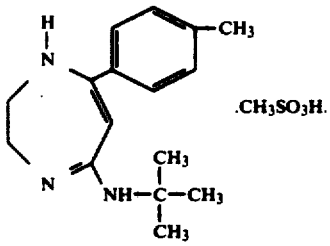

28. The compound according to claim 11 having the formula

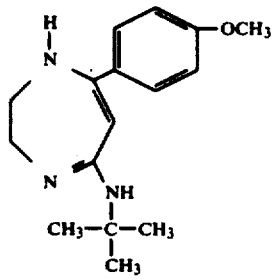

or a pharmaceutically acceptable acid addition salt thereof.

29. The pharmaceutically acceptable acid addition salt according to claim 28 having the formula

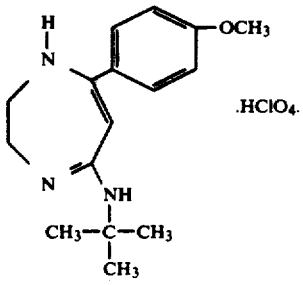

30. The compound according to claim 11 having the formula

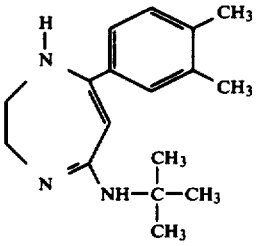

or a pharmaceutically acceptable acid addition salt thereof.

31. The pharmaceutically acceptable acid addition salt according to claim 30 having the formula

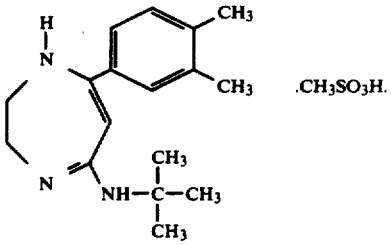

32. The compound according to claim 8 having the formula

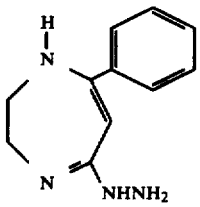

or a pharmaceutically acceptable acid addition salt thereof.

* * * * *